United States Patent [19] [11] 4,233,311
Kramer et al. [45] Nov. 11, 1980

[54] ANTIMICROBIAL AGENTS AND THEIR USE

[75] Inventors: Wolfgang Kramer; Karl H. Büchel; Manfred Plempel; Ingo Haller, all of Wuppertal, Fed. Rep. of Germany

[73] Assignee: Bayer Aktiengesellschaft, Leverkusen, Fed. Rep. of Germany

[21] Appl. No.: 897,900

[22] Filed: Apr. 18, 1978

[30] Foreign Application Priority Data

May 10, 1977 [DE] Fed. Rep. of Germany ....... 2720868

[51] Int. Cl.³ .................. A61K 31/41; A61K 31/415; A61K 31/555

[52] U.S. Cl. ............................... 424/273 R; 424/245; 424/269; 548/101; 548/262; 548/341

[58] Field of Search ............................... 424/273, 245

[56] References Cited

U.S. PATENT DOCUMENTS

| | | | |
|---|---|---|---|
| 3,658,813 | 4/1972 | Godfro et al. | 424/273 X |
| 3,898,341 | 8/1975 | Meiser et al. | 424/273 |
| 3,940,415 | 2/1976 | Büchel et al. | 424/273 X |
| 3,968,229 | 7/1976 | Kramer et al. | 424/273 |
| 3,987,180 | 10/1976 | Büchel et al. | 424/273 |

*Primary Examiner*—Allen J. Robinson
*Attorney, Agent, or Firm*—Sprung, Felfe, Horn, Lynch & Kramer

[57] ABSTRACT

The invention involves the provision of compositions containing a 3,3-dialkyl- or 3-aryl-phenoxy-1-(1,2,4-triazol-1-yl)- and (imidazol-1-yl-alkan-2-ol) ethers which are particularly effective as antimicrobial especially antimycotic, agents. The invention also includes use of said compositions for providing antimicrobial, particularly antimycotic effect.

14 Claims, No Drawings

ANTIMICROBIAL AGENTS AND THEIR USE

The present invention relates to the use as antimicrobial agents, in particular as antimycotics of certain azolyl ether derivatives.

It has already been disclosed that certain azole derivatives, such as, in particular, 3,3-dimethyl-1-phenoxy-1-(1,2,4-triazol-1-yl)- and -imidazol-1-yl-butan-2-ols, have good antimycotic action (compare DT-OS (German Published Specification) No. 2,324,424 [Le A 15 011] and DT-OS (German Published Specification) No. 2,333,355 [Le A 15 145]). However, their action, in particular against dermatophytes and in vivo against Candida, is not always completely satisfactory.

It has been found that compounds which are azolyl ethers of the following general formula or salts or metal complexes thereof

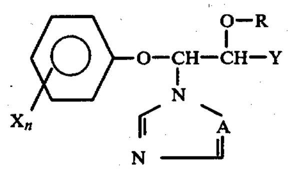

(I)

in which

- A is a CH group or a nitrogen atom,
- R is alkyl, alkenyl, alkinyl, optionally substituted phenyl or optionally substituted benzyl,
- X is halogen, alkyl, alkoxy, alkylthio, alkylsulphonyl, halogenoalkyl, alkoxycarbonyl, nitro, cyano, optionally substituted phenyl, optionally substituted phenoxy or optionally substituted phenylthio,
- Y is optionally substituted alkyl or optionally substituted phenyl and
- n represents an integer having a value of from 0 to 5, have good antimicrobial, in particular antimycotic, properties.

In said formula I, each of said alkyl, alkenyl, alkinyl, alkoxy alkylthio, alkylsulfonyl, halogenoalkyl, alkoxycarbonyl groups can contain, for example, up to 12 carbon atoms.

The compounds of the formula (I) possess two asymmetric carbon atoms; they can therefore exist in the form of the two geometric isomers (erythro form and threo form), which can be obtained in various proportions. In both cases, they exist in the form of optical isomers. It is to be understood that references to compounds of the invention include all the possible isomers unless the contrary is stated.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

Surprisingly, the compounds of the invention exhibit a better antimycotic, therapeutically useful activity than the 3,3-dimethyl-1-phenoxy-1-(1,2,4-triazol-1-yl)- and -imidazol-1-yl-butan-2-ols which are known from the state of the art and which are the most closely related compounds chemically and from the point of view of their action.

The formula (I) provides a general definition of the active compounds which can be used according to the invention. In this formula, X preferably is halogen, in particular fluorine, chlorine or bromine; nitro or cyano; and furthermore, preferably, alkyl, alkoxy, alkylthio, alkylsulphonyl or alkoxycarbonyl having from 1 to 4 carbon atoms in the alkyl moiety in each case, as well as halogenoalkyl having up to 4 carbon atoms and up to 5 halogen atoms, in particular having up to 2 carbon atoms and up to 3 identical or different halogen atoms, each of the halogen atoms being, preferably, fluorine or chlorine, for example, trifluoromethyl. In addition, X preferably is optionally substituted phenyl, phenoxy or phenylthio, preferred substituents being halogen, in particular fluorine, chlorine and bromine; cyano, nitro or halogenoalkyl having up to 2 carbon atoms and up to 3 identical or different halogen atoms, especially fluorine or chlorine, for example trifluoromethyl. The index n preferably represents an integer having a value of from 0 to 3. The radical Y preferably is straight-chain or branched alkyl having from 1 to 9 carbon atoms, optionally mono-substituted or polysubstituted by: halogen, in particular chlorine or bromine; hydroxyl; cyano; a group —CO—$OR^1$, wherein $R^1$ is alkyl having from 1 to 4 carbon atoms; a group —CO—$NR^2R^3$, wherein $R^2$ and $R^3$ are identical or different and each is hydrogen, alkyl having from 1 to 4 carbon atoms or phenyl optionally substituted by halogen; a group —O—CO—$R^4$, wherein $R^4$ is alkyl having from 1 to 18 carbon atoms, halogenoalkyl having from 1 to 4 carbon atoms and from 1 to 3 halogen atoms for example, fluorine or chlorine, phenyl or benzyl, optionally monosubstituted or polysubstituted by halogen, in particular fluorine or chlorine, or cycloalkyl having 5 or 6 carbon atoms. In addition, Y preferably represents optionally monosubstituted or polysubstituted phenyl, preferred substituents being halogen, in particular fluorine, chlorine or bromine. Y particularly preferably represents tert.-butyl, 2,4-dichlorophenyl, 1,1-dimethyl-2-chloro(-bromo)-ethyl or 2-ethoxy(methoxy)-carbonyl-but-2-yl.

R preferably is alkyl, alkenyl or alkinyl having up to 4 carbon atoms in each case, or optionally monosubstituted or polysubstituted benzyl, preferred substituents being: halogen, in particular fluorine, chlorine or bromine, cyano, nitro, alkyl having from 1 to 4 carbon atoms, alkoxycarbonyl having from 1 to 4 carbon atoms in the alkyl moiety or halogenoalkyl having up to 2 carbon atoms and up to 3 halogen atoms, preferably fluorine and/or chlorine, for example, trifluoromethyl. In addition, R preferably represents phenyl optionally substituted by nitro, cyano or alkoxycarbonyl having from 1 to 4 carbon atoms in the alkyl moiety, preferred additional substituents which may be mentioned being: halogen, in particular fluorine, chlorine or bromine, alkyl having from 1 to 4 carbon atoms or halogenoalkyl having up to 2 carbon atoms and up to 3 halogen atoms, preferably fluorine and/or chlorine, for example, trifluoromethyl.

Examples which may be mentioned of particularly active representatives of the active compounds according to the invention, in addition to those disclosed in the preparative examples and the examples in Table 1, are the following: 1-(4-chlorophenoxy)-2-(2,4-dinitrophenoxy)-3,3-dimethyl-1-(1,2,4-triazol-1-yl)-butane, 2-propargyloxy-1(4-chlorophenoxy)-3,3-dimethyl-1-(1,2,4-triazol-1-yl)-butane, 2-propargyloxy-1-(4-chlorophenoxy)-3,3-dimethyl-1-imidazol-1-yl-butane, 2-methoxy-1-(4-cyanophenoxy)-3,3-dimethyl-1-(1,2,4-triazol-1-yl)-butane, 2-methoxy-1-(4-methoxycarbonylphenoxy)-3,3-dimethyl-1-(1,2,4-triazol-1-yl)-butane, 2-methoxy-1-(3-trifluoromethylphenoxy)-3,3-dimethyl-1-(1,2,4-triazol-1-yl)-butane, 2-ethoxy-1-(4-nitrophenoxy)-3,3-dimethyl-1-(1,2,4-triazol-1-yl)-pentane, 2-methoxy-1-(2,4-dichlorophenoxy)-3,3-dimethyl-1-imidazol-1-yl-butane, 2-ethoxy-1-(4-chloro-2-methylphenoxy)-3,3-dimethyl-1-(1,2,4-triazol-1-yl)-butane, 2-ethoxy-1-(4-chlorophenoxy)-3-methyl-3-ethoxycarbonyl-1-(1,2,4-triazol-1-yl)-pentane, 2-allyloxy-1-(4-chlorophenoxy)-3-methyl-3-ethoxycarbonyl-1-imidazol-1-yl-pentane, 2-methoxy-1-(4-chlorophenoxy)-3-butyl-3-methoxycarbonyl-1-imidazol-1-yl-heptane, 2-(2,4-dichlorobenzyloxy)-1-(4-chlorophenoxy)-3-methyl-3-methoxycarbonyl-1-(1,2,4-triazol-1-yl)-hexane, 2-(4-chlorobenzyloxy)-1-(4-chlorophenoxy)-3-benzyl-3-methoxy-carbonyl-1-(1,2,4-triazol-1-yl)-heptane, 2-methoxy-1-(4-chlorophenoxy)-3-methyl-3-chloromethylene-1-(1,2,4-triazol-1-yl)-butane, 2-ethoxy-1-(4-chlorophenoxy)-3-methyl-3-chloromethylene-1-imidazol-1-yl-butane, 2-ethoxy-1-(4-chlorophenoxy)-3-methyl-3-bromomethylene-1-(1,2,4-triazol-1-yl)-butane, 2-ethoxy-1-(4-chlorophenoxy)-3,3-di-chloromethylene-1-(1,2,4-triazol-1-yl)-butane, 2-ethoxy-1-(4-chlorophenoxy)-3,3-dimethyl-4-acetoxy-1-(1,2,4-triazol-1-yl)-butane and 2-allyloxy-1-(4-chlorophenoxy)-3,3-dimethyl-4-hydroxy-1-(1,2,4-triazol-1-yl)-butane.

The active compounds to be used according to the invention and their salts and metal complexes are not yet known. However, they can be prepared by a process in which the alcoholates of 1-azolyl-2-hydroxy-1-phenoxy-alkane derivatives, of the formula

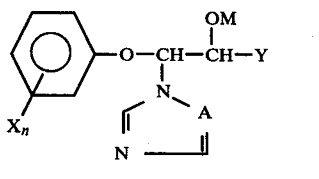

(II)

in which

A, X, Y and n have the same meaning as defined hereinbefore in formula I and

M is an alkali metal or a quaternary ammonium or phosphonium group, are reacted with a halide of the formula R—Hal (III)

in which

R has the same meaning as defined hereinbefore in formula I, and

Hal is chlorine or bromine, in the presence of an inert organic solvent, for example, ethyl ether, preferably, at a temperature of from about 60° to 100° C. In order to isolate the end products, the reaction mixture is freed from the solvent, and water and an organic solvent are added to the residue. The organic phase is then separated off and worked up and purified by conventional methods, and a salt or metal complex is optionally prepared.

In a preferred embodiment, the procedure is appropriately to use a 1-azolyl-2-hydroxy-1-phenoxy-alkane derivative as the starting material, converting the latter into the alkali metal alcoholate of the formula (II) in a suitable inert organic solvent by means of alkali metal hydride or alkali metal amide, and reacting the alkali metal alcoholate immediately, without isolation, with a halide of the formula (III), the compounds of the formula (I) according to the invention being obtained in one operation with the elimination of alkali metal halide.

According to a further preferred embodiment, the preparation of the alcoholates of the formula (II) and the reaction according to the invention are appropriately carried out in a two phase system, such as, for example, aqueous sodium hydroxide solution or potassium hydroxide solution/toluene or methylene chloride, with the addition of from 0.01 to 1 mol of a phase transfer catalyst, such as, for example, an ammonium or phosphonium compound, the alcoholate being formed in the organic phase or at the interface and being reacted with the halide present in the organic phase.

The alcoholates of the formula (II) are not known. They are obtained when the corresponding 1-azolyl-2-hydroxy-1-phenoxy-alkane derivatives are reacted with suitable strong bases, such as alkali metal amides or hydrides or quaternary ammonium hydroxides or phosphonium hydroxides, in an inert solvent. Some of the said 1-azolyl-2-hydroxy-1-phenoxyalkane derivatives are known (compare DT-OS (German Published Specification) 2,324,010 corresponding to U.S. Pat. No. 3,952,002 dated Apr. 20, 1976 and DT-OS (German Published Specification) No. 2,333,354 corresponding to U.S. Pat. No. 3,940,414 dated Feb. 24, 1976) and some are the subject of pending applications of common assignment applications P-2,632,603 of July 20, 1976, corresponding U.S. application Ser. No. 816,975, filed July 9, 1977, P-2,632,602 of July 20, 1976, P-2,635,663 of Aug. 7, 1976 corresponding to U.S. application Ser. No. 819,533, filed July 27, 1977, P-2,635,666 of Aug. 7, 1976 corresponding to U.S. application Ser. No. 819,534 filed July 27, 1977, P-2,705,677 of Feb. 11, 1977 corresponding to U.S. application Ser. No. 872,987, filed Jan. 27, 1978, and P-2,705,678 of Feb. 11, 1977 corresponding to U.S. application Ser. No. 872,988, filed Jan. 27, 1978). The alcoholates are obtained by reducing the corresponding azolylalkanone derivatives of the formula

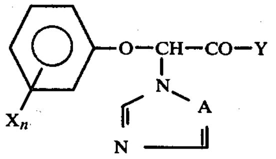

(IV)

in which

A, X, Y and n have the same meaning as defined hereinbefore in formula I, by means of a complex hydride, such as lithium aluminum hydride or sodium borohydride, by means of aluminium isopropylate, or with formamidinesulphonic acid and alkali metal hydroxide in a manner which is generally known.

Some of the compounds of the formula (IV) are also known (compare DT-OS (German Published Specification) No. 2,201,063 corresponding to U.S. Pat. No. 3,912,752 dated Oct. 14, 1975 and DT-OS (German Published Specification) No. 2,325,156 corresponding to U.S. Pat. No. 3,898,341 dated Aug. 5, 1975), and some are the subject of the above-mentioned pending applications of common assignment. They are obtained by reacting a halogenoketone of the formula (V)

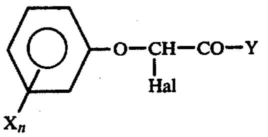

in which

X, Y and n have the same meaning as defined hereinbefore in formula I and

Hal is chlorine or bromine, with a known azole of the formula (VI)

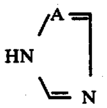

in which

A has the same meaning as defined hereinbefore in formula I, in the presence of a diluent and an acid-binding agent.

The halogenoketones of the formula (V) are known (compare the above mentioned German Offenlegunsschriften (German Published Specifications)), or they are the subject of the above mentioned pending patent applications. They can be prepared, for example, by a process in which a known phenol of the formula (VII)

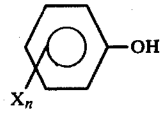

in which

X and n have the same meaning as defined hereinbefore in formula I, is reacted with a known halogenoketone of the formula $$Hal-CH_2-CO-Y \quad (VIII)$$

in which

Y has the same meaning as defined hereinbefore in formula I, and

Hal is chlorine or bromine.

The active hydrogen atom which still remains is then replaced by halogen in the customary manner (compare also the preparation examples).

The starting materials of the formula (III) are generally known compounds of organic chemistry.

Among the salts and metal complexes of the invention those salts and metal complexes that are pharmaceutically acceptable are particularly important and are preferred.

Suitable salts include, preferably, those with the hydrogen halide acids, such as, for example, hydrochloric acid and hydrobromic acid, especially hydrochloric acid, phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The free azolyl ethers of the general formula I and their salts and metal complexes can be interconverted in any suitable manner; methods for such interconversion are known in the art.

The salts of the azolyl ethers of the formula (I) can be obtained in a simple manner by customary salt formation methods, for example by dissolving the base in ether, for example diethyl ether, and adding the acid, for example nitric acid, and can be isolated in a known manner, for example by filtration, and optionally purified.

Compounds which can be used for the preparation of metal salt complexes of the compounds of the formula (I) are preferably salts of metals of main groups II to IV and of sub-groups I and II as well as IV to VIII of the Periodic Table of elements, and copper, zinc, manganese, magnesium, tin, iron and nickel may be mentioned as examples of such metals. Preferred anions of the salts are those which are derived from physiologically acceptable acids. These include, preferably, the hydrogen halide acids, such as, for example, hydrochloric acid, and furthermore phosphoric acid, nitric acid and sulphuric acid.

The metal complexes of the compounds of the formula (I) can be obtained in a simple manner by conventional processes, thus, for example, by dissolving the metal salt in an alcohol, for example ethanol, and adding the resulting solution to the compound of the formula (I). The metal salt complexes can be isolated in a known manner, for example, by filtration, and optionally purified by recrystallisation.

The compounds of the formula (I) which can be used according to the invention, and their salts, display antimicrobial, in particular powerful antimycotic actions. They possess a very broad spectrum of antimycotic activity, especially against dermatophytes and blastomyces as well as biphase fungi, for example, against Candida species, such as Candida albicans, Epidermophyton species, such as Epidermophyton floccosum, Aspergillus species, such as Aspergillus niger and Aspergillus fumigatus, Trichophyton species, such as Trichophyton mentagrophytes, Microsporon species, such as Microsporon felineum and Penicillium species, such as Penicillium commune. The recital of these micro-organisms in no way implies a limitation of the germs which can be combated but is only of illustrative character.

Examples which may be mentioned of fields of indication in medicine are: dermatomycoses and systemic mycoses caused by Trichophyton mentagrophytes and other Trichophyton species, Microsporon species, Epidermophyton floccosum, blastomyces and biphase fungi as well as moulds.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions, can for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecuar weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 500 mg to 15 g, most preferably from 2.5 g to 10 g, of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above mentioned diseases in warm-blooded animals, which comprises administering to the said animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably parenterally, most preferably intravenously. Preferred pharmaceutical compositions and medicaments are therefore those adapted for parenteral adminstration, such as injection solutions and suspensions and ampoules thereof. Administration in the method of the invention is preferably parenterally, most preferably intravenously.

In general it has proved advantageous to administer amounts of from 10 mg to 300 mg, most preferably from 50 to 200 mg, per kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

EXAMPLE A

Antimycotic in vitro activity

Description of the experiment:

The in vitro tests were carried out in a series dilution test with germ inocula of an average of $5\times10^4$ germs/ml of substrate. The nutrient medium was (a) for dermatophytes and moulds: Sabouraud's milieu d'epreuve and (b) for yeasts: meat extract/glucose broth.

The incubation temperature was 28° C. and the duration of incubation was 24 to 96 hours.

TABLE A:

Antimycotic in vitro activity

| | MINIMUM INHIBITORY CONCENTRATION VALUES in γ/ml of nutrient medium for | | | | | |
|---|---|---|---|---|---|---|
| Active compound | *Trichophyton mentagr.* | *Candida albicans* | *Penicillium commune* | *Aspergillus species* | *Microsporon felineum* | *Torulopsis glabrata* |
| 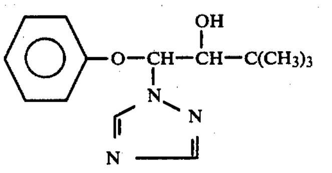 (known) | 32 | 64 | >64 | >64 | — | — |
| 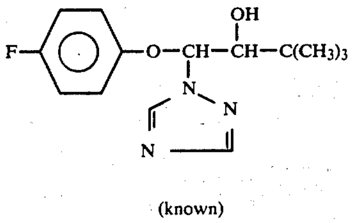 (known) | 4 | 64 | >64 | >64 | 64 | — |
| 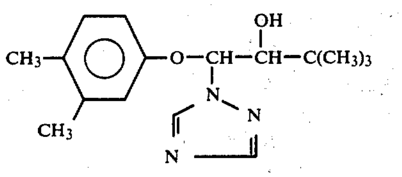 (known) | 4 | >64 | >64 | >64 | 64 | — |

TABLE A:-continued

Antimycotic in vitro activity

| Active compound | MINIMUM INHIBITORY CONCENTRATION VALUES in γ/ml of nutrient medium for *Trichophyton mentagr.* | *Candida albicans* | *Penicillium commune* | *Aspergillus species* | *Microsporon felineum* | *Torulopsis glabrata* |
|---|---|---|---|---|---|---|
| 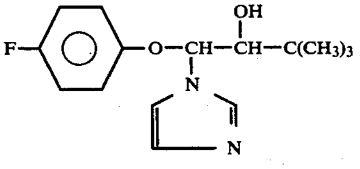 (known) | 64 | 64 | >64 | — | — | — |
| 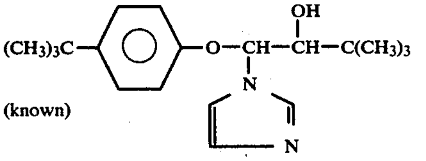 (known) | 32 | >64 | >64 | >64 | — | — |
| 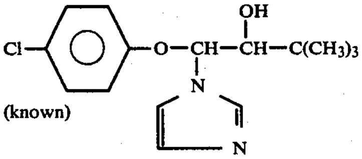 (known) | 1 | >64 | >64 | >64 | 32 | — |
| Compounds from Example No. | | | | | | |
| 4 | 1 | 32 | — | 32 | 32 | 8 |
| 11 | 4 | 32 | — | 32 | 32 | 32 |
| 25 | <1 | 64 | — | 4 | 32 | — |
| 30 | <1 | 32 | — | 32 | 32 | 32 |
| 34 | <1 | 64 | 8 | 32 | 4 | — |
| 36 | <1 | 32 | 32 | 8 | 8 | 4 |
| 37 | <1 | 32 | — | 8 | 4 | 1 |
| 38 | <1 | 8 | — | 8 | 4 | 4 |
| 39 | <1 | 32 | — | 32 | 4 | 8 |
| 40 | <1 | 8 | — | 32 | 4 | 4 |
| 43 | <1 | 32 | — | 32 | 8 | 8 |
| 55 | <1 | 8 | — | 32 | 8 | 8 |
| 56 | <1 | 8 | — | 32 | 16 | 64 |
| 57 | <1 | 32 | — | 4 | 4 | 1 |

EXAMPLE B

Antimycotic in vivo activity (oral) in candidosis of mice

Description of the experiment:

Mice of the type SPF-$CF_1$ were infected intravenously with 1-2×$10^6$ logarithmically growing Candida cells, which were suspended in physiological sodium chloride solution. The animals were treated orally one hour before and seven hours after the infection with, in each case, 100 mg/kg of body weight of the fomulations.

Untreated animals died from the infection 3 to 6 days after infection. The survival rate on the 6th day after infection was about 5% in the case of untreated control animals.

| Explanation of symbols: | | |
|---|---|---|
| +++++ | = very good action | = ≧ 90% of survivors on the 6th day after infection |
| ++++ | = good action | = ≧ 80% of survivors on the 6th day after infection |
| +++ | = action | = ≧ 60% of survivors on the 6th day after infection |
| ++ | = poor action | = ≧ 40% of survivors on the 6th day after infection |
| + | = trace of action | |
| n.a. | = no action | |

TABLE B:

Antimycotic in vivo activity (oral) in candidosis of mice

| Active compound | Action |
|---|---|
| 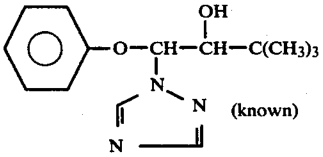 (known) | n.a. |

TABLE B:-continued

| Antimycotic in vivo activity (oral) in candidosis of mice | |
|---|---|
| Active compound | Action |
| 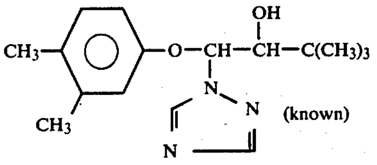 (known) | n.a. |
| 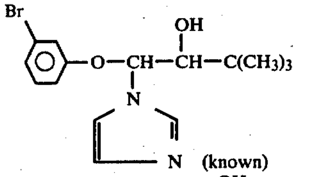 (known) | n.a. |
| 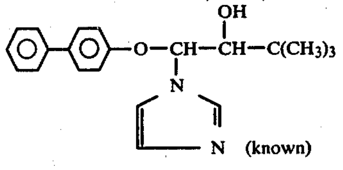 (known) | n.a. |
| Compounds from Example No. | |
| 1 | + |
| 4 | + |
| 8 | + |
| 9 | +++++ |
| 13 | ++++ |
| 22 | ++ |
| 36 | ++++ |
| 37 | +++++ |
| 38 | ++++ |
| 39 | ++++ |
| 40 | +++++ |
| 41 | +++ |
| 43 | ++ |
| 47 | +++++ |
| 48 | ++ |
| 49 | +++ |
| 56 | +++++ |

PREPARATION EXAMPLES

EXAMPLE 1

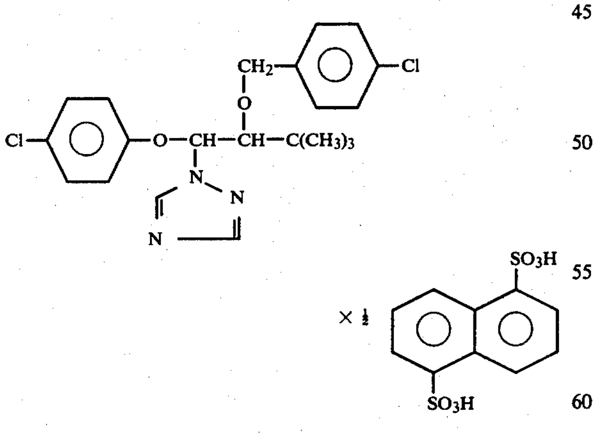

A mixture of 900 ml of 33% strength sodium hydroxide solution, 75 ml of 50% strengh zephirol solution (butyl-dimethyl-dodecyl-ammonium salt) and 242 g (1.5 moles) of p-chlorobenzyl chloride is added dropwise to 222 g (0.75 mol) of 1-(4-chlorophenoxy)-3,3-dimethyl-1-(1,2,4-triazol-1-yl)-butan-2-ol in 700 ml of toluene. The mixture is stirred at 80° C. for 16 hours. After cooling, the organic phase is separated off and washed with 2 l of 5% strength hydrochloric acid, dried over sodium sulphate and concentrated in vacuo by distilling off the solvent. The oil which remains is taken up in 1.2 l of acetone, and a solution of 100 g of 1,5-naphthalenedisulphonic acid in 500 ml of acetone is added. The crystalline precipitate is filtered off, washed with 1,000 ml of acetone and dried at 50° C. over phosphorus pentoxide in vacuo. This gives 280 g (66% of theory) of 2-(4-chlorobenzyloxy)-1-(4-chlorophenoxy)-3,3-dimethyl-1-(1,2,4-triazol-1-yl)-butane 1,5-naphthalenedisulphonate of melting point 190° C.

Preparation of the precursors

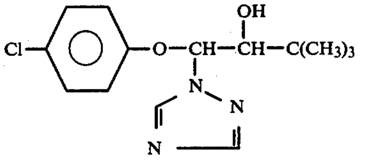

587 g (2 mols) of 1-(4-chlorophenoxy)-3,3-dimethyl-1-(1,2,4-triazol-1-yl)-butan-2-one are dissolved in 3 l of methanol. A total of 80 g (2 mols) of sodium borohydride are added in portions of 5 g each to the solution at 0° to 10° C. whilst stirring and cooling with ice, and the mixture is stirred at 5° to 10° C. for 2 hours and thereafter at room temperature for 12 hours. It is then cooled to 10° C. and 300 g (3 mols) of concentrated aqueous hydrochloric acid are added at 10° to 20° C. After stirring at room temperature for 6 hours, the resulting suspension is diluted with 3.8 l of water, which contains 400 g (4.8 mols) of sodium bicarbonate. The precipitate thereby formed is filtered off. This gives 502 g (85% of theory) of 1-(4-chlorophenoxy)-3,3-dimethyl-1-(1,2,4-triazol-1-yl)-butan-2-ol of melting point 112°-117° C.

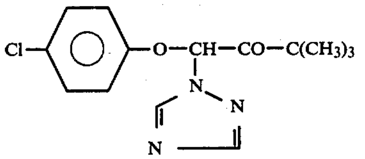

418 g (6.6 mols) of 1,2,4-triazole are dissolved in 3,000 ml of acetone. 934 g (7.2 mols) of anhydrous, powdered potassium carbonate are added to this solution, the suspension is heated to the boil and a solution of 1,565 L g (6 mols) of 1-(4-chlorophenoxy)-1-chloro-3,3-dimethyl-butan-2-one in 1,500 ml of acetone is added dropwise in a manner such that the mixture boils under reflux without being heated. After the addition has ended, the mixture is heated under reflux for 15 hours in order to bring the reaction to completion; the resulting precipitate is then filtered off, washed with acetone and discarded. The filtrate is freed from solvent under a water pump vacuum, the residue is taken up in 3,000 ml of toluene and the toluene solution is washed once with a solution of 100 g of 37% strength hydrochloric acid in 2,000 ml of water. The aqueous phase is separated off and discarded; the organic phase is washed with 5,000 ml of water and, after adding a further 4,000 ml of toluene, is stirred with a solution of 145 g of sodium hydroxide in 3,500 ml of water at room temperature for 6 hours. Thereafter, the organic phase is separated off, washed with water until neutral and freed from solvent under a water pump vacuum. This gives 1,535 g (87% of theory) of 1-(4-chlorophenoxy)-3,3-dimethyl-1-(1,2,4-triazol-1-yl)-butan-2-one of melting point 75°-76° C.

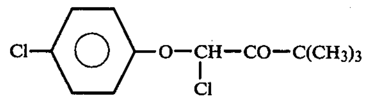

771 g (6 mols) of 4-chlorophenol are dissolved in 3,600 ml of acetone. 3 g of anhydrous sodium iodide and 910 g (6.6 mols) of anhydrous, powdered potassium carbonate are introduced, and 895 g (6.3 mols) of 94.6% pure monochloropinacoline are added dropwise under reflux. After stirring the mixture at the reflux temperature for 20 hours, the precipitate is filtered off, washed with acetone and discarded. The filtrate is freed from the solvent under a water pump vacuum. The resulting white residue is taken up in 3,000 ml of carbon tetrachloride and the carbon tetrachloride solution is warmed to 60° C. 891 g (6.6 mols) of sulphuryl chloride are added dropwise to this solution, without further warming, in a manner such that continuous evolution of gas takes place. After the addition has ended, the mixture is heated under reflux for 15 hours. Finally, the solvent is distilled off under a water pump vacuum. This gives 1,565 g of 1-(4-chlorophenoxy)-1-chloro-3,3-dimethyl-butan-2-one in quantitative yield, which can be used without further purification for the reaction described above.

EXAMPLE 2

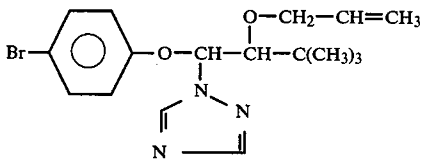

34 g (0.1 mol) of 1-(4-bromophenoxy)-3,3-dimethyl-1-(1,2,4-triazol-1-yl)-butan-2-ol are suspended in 175 ml of dioxane and the suspension is added dropwise to a mixture of 3.5 g of 80% strength sodium hydride and 125 ml of dioxane, whilst stirring. Thereafter, the mixture is heated under reflux for one hour. After cooling, 14.5 g (0.12 mol) of allyl bromide are added dropwise at room temperature to the sodium salt thus obtained. The mixture is then heated under reflux for 15 hours, allowed to cool, and is concentrated by distilling off the solvent. The oily residue is taken up in 600 ml of methylene chloride and the methylene chloride solution is washed twice with 1,000 ml of water each time, dried over sodium sulphate and concentrated. The residue is distilled under a high vacuum. This gives 30 g (79% of theory) of 2-allyloxy-1-(4-bromophenoxy)-3,3-dimethyl-1-(1,2,4-triazol-1-yl)-butane of boiling point 152°-154° C./0.2 mm.

EXAMPLE 3

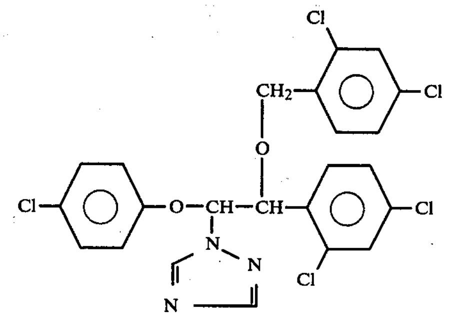

19.2 g (0.05 mol) of 1-(4-chlorophenoxy)-2-(2,4-dichlorophenyl)-1-(1,2,4-triazol-1-yl)-ethan-2-ol are dissolved in 100 ml of dioxane and the solution is added dropwise to a mixture of 2 g of 80% strength sodium hydride in 100 ml of dioxane at 80° C. After the evolution of hydrogen has subsided, 10 g (0.05 mol) of 2,4-dichlorobenzyl chloride are added dropwise and the mixture is heated under reflux for 15 hours. After cooling, the solvent is distilled off in vacuo and the residue is taken up in 100 ml of water and 100 ml of methylene chloride. The organic phase is separated off, washed twice with 100 ml of water each time, dried over sodium sulphate and concentrated in vacuo by distilling off the solvent. The solid residue is recrystallised from ether. This gives 9 g (31% of theory) of 1-(4-chlorophenoxy)-2-(2,4-dichlorobenzoyloxy)-2-(2,4-dichlorophenyl)-1-(1,2,4-triazol-1-yl)-ethane of melting point 132°-135° C.

EXAMPLE 4

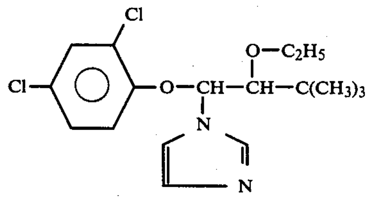

53 g (0.1 mol) of 1-(2,4-dichlorophenoxy)-3,3-dimethyl-1-imidazol-1-yl-butan-2-ol are dissolved in 150 ml of dioxane and the solution is added dropwise to 3.5 g of 80% strength sodium hydride solution in 150 ml of dioxane. The mixture is stirred for 3 hours at room temperature and then 13,1 g (0,12 mols) ethyl bromide are added. The mixture is stirred under reflux for 17 hours. After cooling, the solvent is distilled off in vacuo, the residue is taken up in 600 ml of methylene chloride and the methylene chloride solution is washed twice with 1,000 ml of water each time, dried over sodium sulphate and distilled under a high vacuum. This gives 10 g (28% of theory) of 2-ethoxy-1-(2,4-dichlorophenoxy)-3,3-dimethyl-1-imidazol-1-yl-butane of boiling point 170°-175° C./0.2 mm.

The following examples in Table 1 are obtainable analogously.

TABLE 1

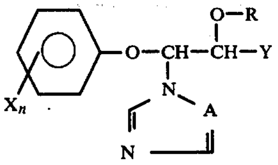

| Ex. No. | A | R | $X_n$ | Y | Melting point in °C. or boiling point in °C./mm Hg column |
|---|---|---|---|---|---|
| 5 | N | $-CH_2-CH=CH_2$ | 4-Cl | $C(CH_3)_3$ | 140–45 (xHCl) |
| 6 | N | $-CH_2-CH=CH_2$ | 4-Cl | 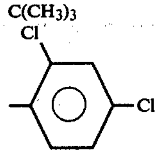 | 164–66 (xHCl) |
| 7 | N | 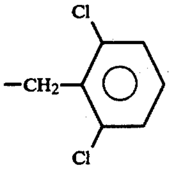 | 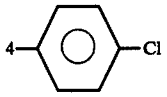 | $C(CH_3)_3$ | 137–45 |
| 8 | N | 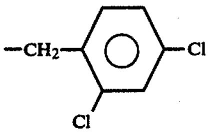 | 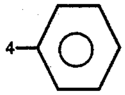 | $C(CH_3)_3$ | 96 |
| 9 | N | $CH_3$ | 4-Cl | $C(CH_3)_3$ | viscous oil |
| 10 | N | $C_2H_5$ | 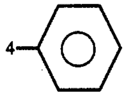 | $C(CH_3)_3$ | viscous oil |
| 11 | N | $C_2H_5$ | 2,4-$Cl_2$ | $C(CH_3)_3$ | 145–58/0.2 |
| 12 | N | $-CH_2-CH=CH_2$ | 2,4-$Cl_2$ | $C(CH_3)_3$ | 169–74/0.2 |
| 13 | N | $C_2H_5$ | 4-Cl | $C(CH_3)_3$ | viscous oil |
| 14 | N | 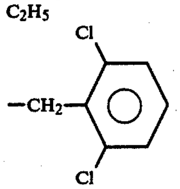 | 2,4-$Cl_2$ | $C(CH_3)_3$ | 285(x½ NDS) |
| 15 | N | $C_2H_5$ | 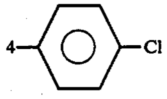 | $C(CH_3)_3$ | viscous oil |
| 16 | N | $-CH_2-CH=CH_2$ | 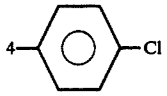 | $C(CH_3)_3$ | 89–91 |
| 17 | N | 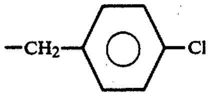 | 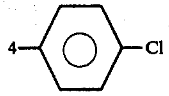 | $C(CH_3)_3$ | 152 (xHCl) |
| 18 | N | $-CH_2-CH=CH_2$ | 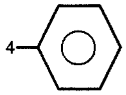 | $C(CH_3)_3$ | 197/0.2 |
| 19 | N | 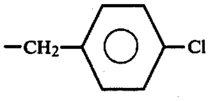 | 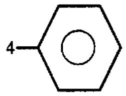 | $C(CH_3)_3$ | 134–38 (xHCl) |
| 20 | N | 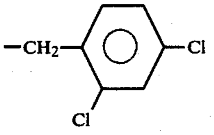 | 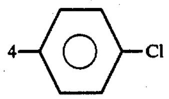 | $C(CH_3)_3$ | 154–57 |

TABLE 1-continued
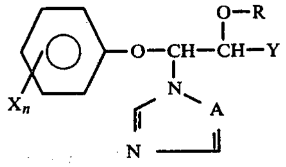
| Ex. No. | A | R | $X_n$ | Y | Melting point in °C. or boiling point in °C./mm Hg column |
|---|---|---|---|---|---|
| 21 | N | $CH_3$ | 2,4-$Cl_2$ | $C(CH_3)_3$ | viscous oil |
| 22 | N | $C_2H_5$ | 4-Br | $C(CH_3)_3$ | 154–58/0.2 |
| 23 | N | 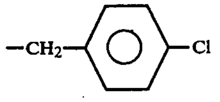 | 4-Br | $C(CH_3)_3$ | 175–77 (x½ NDS) |
| 24 | N | 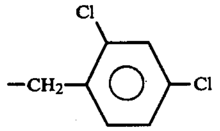 | 4-Br | $C(CH_3)_3$ | 176–79 (x½ NDS) |
| 25 | N | $CH_3$ | 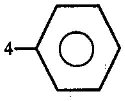 | $C(CH_3)_3$ | 119–21 (Form A) |
| 26 | N | $CH_3$ | 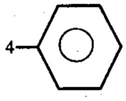 | $C(CH_3)_3$ | 96 |
| 27 | N | 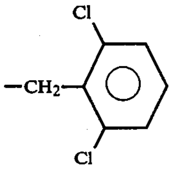 | 4-Br | $C(CH_3)_3$ | 192–98 (x½ NDS) |
| 28 | N | $CH_3$ | 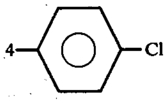 | $C(CH_3)_3$ | 180–86 (x½ NDS) |
| 29 | N | $CH_3$ | 4-Br | $C(CH_3)_3$ | 155–58/0.2 |
| 30 | N | 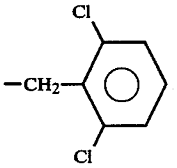 | 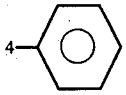 | $C(CH_3)_3$ | 132–42 (xHCl) |
| 31 | N | 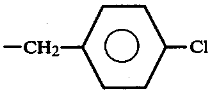 | 2,4-$Cl_2$ | $C(CH_3)_3$ | 194–96 (x½ NDS) |
| 32 | N | 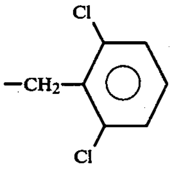 | 4-Cl | $C(CH_3)_3$ | 190 (x½ NDS) |
| 33 | N | 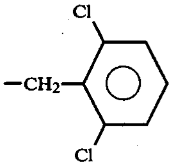 | 4-Cl | $C(CH_3)_3$ | 116 |

TABLE 1-continued

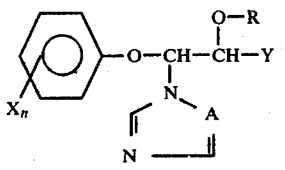

| Ex. No. | A | R | $X_n$ | Y | Melting point in °C. or boiling point in °C./mm Hg column |
|---|---|---|---|---|---|
| 34 | CH | 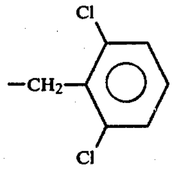 | 4-Cl | $C(CH_3)_3$ | 197–205 (xHCl) |
| 35 | CH | 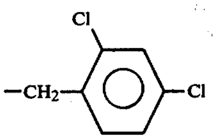 | 4-Cl | $C(CH_3)_3$ | 213–15 (xHCl) |
| 36 | CH | $CH_3$ | 4-Cl | $C(CH_3)_3$ | viscous oil |
| 37 | CH | $C_2H_5$ | 4-Cl | $C(CH_3)_3$ | viscous oil |
| 38 | CH | $C_2H_5$ | 4-Br | $C(CH_3)_3$ | 166–68/0.2 |
| 39 | CH | $-CH_2-CH=CH_2$ | 4-Br | $C(CH_3)_3$ | 170–73/0.2 |
| 40 | CH | $-CH_2-CH=CH_2$ | 4-Cl | $C(CH_3)_3$ | 164–66/0.2 |
| 41 | CH | 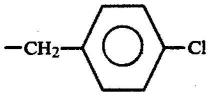 | 4-Cl | $C(CH_3)_3$ | 211–16 (x½ NDS) |
| 42 | CH | 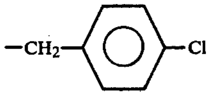 | 4-Br | $C(CH_3)_3$ | 227–30 (x½ NDS) |
| 43 | CH | $-CH_2-CH=CH_2$ | 2,4-$Cl_2$ | $C(CH_3)_3$ | 181–85 |
| 44 | CH | 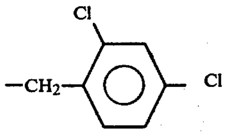 | 2,4-$Cl_2$ | $C(CH_3)_3$ | 210–20 (x½ NDS) decomposition |
| 45 | CH | 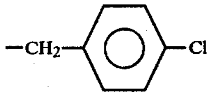 | 2,4-$Cl_2$ | $C(CH_3)_3$ | 250 (x½ NDS) |
| 46 | CH | 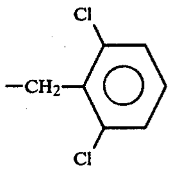 | 2,4-$Cl_2$ | $C(CH_3)_3$ | 238–42 (x½ NDS) |
| 47 | CH | $C_2H_5$ | 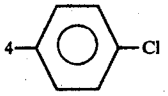 | $C(CH_3)_3$ | 240 (x½ NDS)(A-form) |
| 48 | CH | $C_2H_5$ | 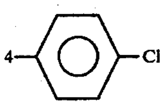 | $C(CH_3)_3$ | 246 (x½ NDS)(B-form) |
| 49 | CH | $-CH_2-CH=CH_2$ | 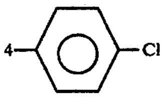 | $C(CH_3)_3$ | 247 (x½ NDS) |

TABLE 1-continued
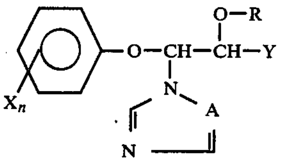
| Ex. No. | A | R | $X_n$ | Y | Melting point in °C. or boiling point in °C./mm Hg column |
|---|---|---|---|---|---|
| 50 | CH | 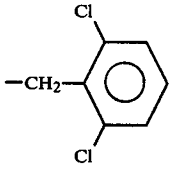 | 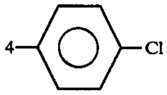 | $C(CH_3)_3$ | 174–76 (x½ NDS) |
| 51 | CH | 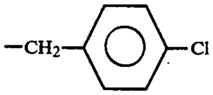 | 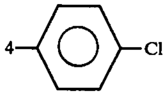 | $C(CH_3)_3$ | 228–32 (x½ NDS) (A-form) |
| 52 | CH | 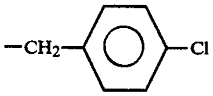 | 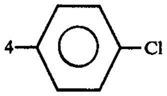 | $C(CH_3)_3$ | 170–73 (x½ NDS) (B-form) |
| 53 | CH | 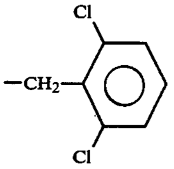 | 4-Br | $C(CH_3)_3$ | 249–50 (x½ NDS) |
| 54 | CH | 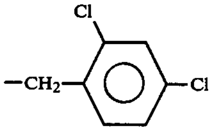 | 4-Br | $C(CH_3)_3$ | 212 (xHCl) |
| 55 | CH | $CH_3$ | 2,4-$Cl_2$ | $C(CH_3)_3$ | 165–68/0.2 |
| 56 | CH | $CH_3$ | 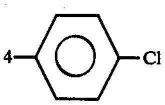 | $C(CH_3)_3$ | 230–32 (x½ NDS) |
| 57 | CH | $CH_3$ | 4-Br | $C(CH_3)_3$ | 169–74/0.35 |
| 58 | $CH_3$ | 4-Cl | 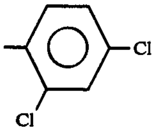 | 200–12 (x½ NDS) | |
| 59 | CH | $CH_3$ | 4-Cl | 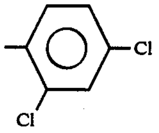 | |
| 60 | CH | $C_2H_5$ | 4-Cl | 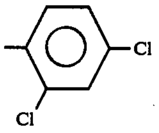 | |
| 61 | CH | $-CH_2-CH=CH_2$ | 4-Cl | 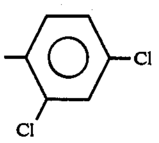 | |

TABLE 1-continued
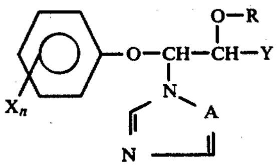
| Ex. No. | A | R | $X_n$ | Y | Melting point in °C. or boiling point in °C./mm Hg column |
|---|---|---|---|---|---|
| 62 | CH | $-CH_2-C\equiv CH$ | 4-Cl | 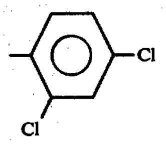 | |
| 63 | CH | 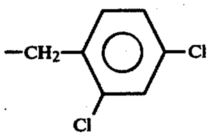 | 4-Cl | 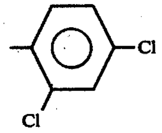 | |
| 64 | CH | $CH_3$ | 2,4-$Cl_2$ | 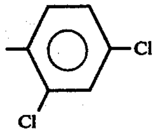 | |
| 65 | CH | $C_2H_5$ | 2,4-$Cl_2$ | 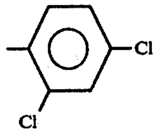 | |
| 66 | CH | n-$C_3H_7$ | 2,4-$Cl_2$ | 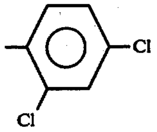 | |
| 67 | N | $C_2H_5$ | 4-Cl | 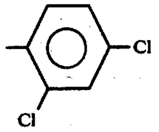 | 162-65 (xHCl) |
| 68 | N | $-CH_2-C\equiv CH$ | 4-Cl | 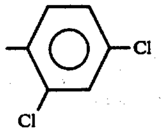 | |
| 69 | N | $CH_3$ | 2,4-$Cl_2$ | 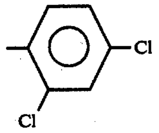 | 140-48 (xHCl) |
| 70 | N | $C_2H_5$ | 2,4-$Cl_2$ | 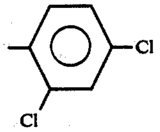 | |
| 71 | N | n-$C_3H_7$ | 2,4-$Cl_2$ | 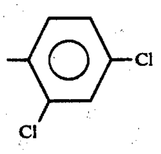 | |

TABLE 1-continued

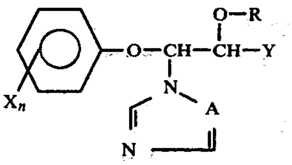

| Ex. No. | A | R | $X_n$ | Y | Melting point in °C. or boiling point in °C./mm Hg column |
|---|---|---|---|---|---|
| 72 | N | $CH_3$ | 4-F | 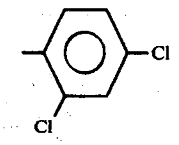 | 220 (xHCl) |
| 73 | N | $C_2H_5$ | 4-F | 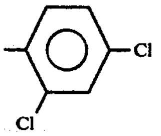 | |
| 74 | N | 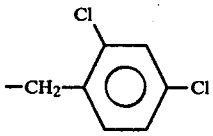 | 4-F | 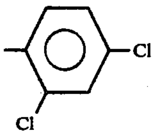 | |
| 75 | CH | $C_2H_5$ | 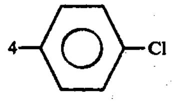 | $C(CH_3)_3$ | 211 (xHCl)(A-form) |
| 76 | CH | $-CH_2-CH=CH_2$ | 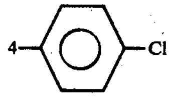 | $C(CH_3)_3$ | 200 (xHCl)(A-form) |
| 77 | N | 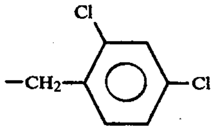 | 4-Cl | $C(CH_3)_3$ | 75–77 (A-form) |
| 78 | N | $-CH_2-O-Cl$ | 4-Cl | $C(CH_3)_3$ | 84–86 (A-form) |
| 79 | N | $CH_3$ | 4-Cl | $C(CH_3)_3$ | 63–66 (A-form) |
| 80 | N | $CH_3$ | 4-Cl | $C(CH_3)_3$ | Oil (B-form) |
| 81 | CH | $CH_3$ | 4-Cl | $C(CH_3)_3$ | 188–92 (xHCl) |

NDS = 1,5-naphthalenedisulphonic acid
A and B form = in each case one of the two possible geometric isomers

What we claim is:

1. A pharmaceutical composition containing as an active ingredient on antimycotically effective amount of a compound which is an azolyl ether of the following formula, or its salt or a metal complex thereof

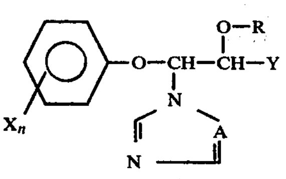

(I)

in which

A is a CH group,

R is alkyl, alkenyl or alkinyl, each having up to 4 carbon atoms, phenyl or benzyl, each being optionally mono- or poly-substituted by halogen, cyano, nitro, alkyl having from 1 to 4 carbon atoms, alkoxy-carbonyl having from 1 to 4 carbon atoms in the alkyl moiety, and halogenoalkyl having up to 2 carbon atoms and up to 3 halogen atoms, X is halogen, alkyl, alkoxy, alkylthio, alkylsulphonyl, halogenoalkyl or alkoxycarbonyl, each having up to 4 carbon atoms in the alkyl moiety, nitro, cyano, or phenyl, phenoxy or phenylthio, each optionally substituted by halogen, cyano, nitro or halogenoalkyl having up to 2 carbon atoms and up to 3 halogen atoms, Y is a straight-chain or branched alkyl having from 1 to 9 carbon atoms and optionally mono- or poly-substituted by halogen, hydroxyl, cyano, —CO—OR[1] wherein $R^1$ is alkyl having from 1 to 4 carbon atoms, —CO—NR[2]R[3] wherein $R^2$ and $R^3$ are the same or different and each is hydrogen, alkyl having from 1 to 4 carbon atoms, or phenyl optionally substituted by halogen, —O—CO—R[4] wherein $R^4$ is alkyl having from 1 to 18 carbon atoms, halogenoalkyl having from 1 to 4 carbon atoms and from 1 to 3 halogen atoms, phenyl or benzyl each optionally mono- or poly-substituted by halogen or cycloalkyl having 5 or 6 carbon atoms; or phenyl optionally mono- or poly-substituted by halogen, and n represents an integer having a value of from 0 to 5, in admixture with a solid, liquid or liquefied gaseous diluent.

2. A composition according to claim 1 in which the active ingredient is a compound as defined in claim 1 in which X is fluorine, chlorine, bromine, nitro, cyano, alkyl having 1 to 4 carbon atoms, alkoxy, alkylthio, alkylsulphonyl or alkoxycarbonyl each having from 1 to 4 carbon atoms in the alkyl moiety, halogenalkyl having up to 4 carbon atoms and up to 5 halogen atoms, or phenyl, phenoxy or phenylthio each optionally substituted by halogen, cyano, nitro or halogenoalkyl having up to 2 carbon atoms and up to 3 halogen atoms;

n represents an integer having a value of from 0 to 3;

Y is straight-chain or branched alkyl having from 1 to 9 carbon atoms and optionally mono- or poly-substituted by halogen, hydroxyl, cyano, —CO—$OR^1$ wherein $R^1$ is alkyl having from 1 to 4 carbon atoms, —CO—$NR^2R^3$ wherein $R^2$ and $R^3$ are the same or different and each is hydrogen, alkyl having from 1 to 4 carbon atoms, or phenyl optionally substituted by halogen, —O—CO—$R^4$ wherein $R^4$ is alkyl having from 1 to 18 carbon atoms, halogenoalkyl having from 1 to 4 carbon atoms and from 1 to 3 halogen atoms, phenyl or benzyl each optionally mono- or poly-substituted by halogen or cycloalkyl having 5 or 6 carbon atoms; or phenyl optionally mono- or poly-substituted by halogen; and R is alkyl, alkenyl or alkinyl, each having up to 4 carbon atoms, or benzyl or phenyl, each being optionally mono- or poly-substituted by halogen, cyano, nitro, alkyl having from 1 to 4 carbon atoms, alkoxy-carbonyl having from 1 to 4 carbon atoms in the alkyl moiety, and halogenalkyl having up to 2 carbon atoms and up to 3 halogen atoms.

3. A composition according to claim 1 in which the active ingredient is the compound 2-ethoxy-1-(4-chlorophenyloxy)-3,3-dimethyl-1-(imidazol-1-yl)-butane.

4. A composition according to claim 1 in which the active ingredient is the compound 2-allyloxy-1-(4-chlorophenyloxy)-3,3-dimethyl-1-(imidazol-1-yl)-butane.

5. A composition according to claim 1 in which the active ingredient is the compound 2-ethoxy-1-(4′-chlorobiphenyloxy)-3,3-dimethyl-1-(imidazol-1-yl)-butane.

6. A composition according to claim 1 in which the active ingredient is the compound 2-methoxy-1-(4′-chlorobiphenyloxy)-3,3-dimethyl-1-(imidazol-1-yl)-butane.

7. A pharmaceutical composition of claim 1 in the form of a sterile or isotonic aqueous solution.

8. A composition according to claim 1 containing from 0.5 to 95% of the said active ingredient, by weight.

9. A medicament in dosage unit form comprising an antimycotically effective amount of a compound of claim 1 together with an inert pharmaceutical carrier.

10. A medicament of claim 9 in the form of tablets, pills, dragees, capsules, ampoules, or suppositories.

11. A method of combating mycoses in warm-blooded animals which comprises administering to the said animals an antimycotically effective amount of a composition as defined in claim 1.

12. A method according to claim 11 in which the active compound is administered in an amount of 10 to 300 mg per kg body weight per day.

13. A method according to claim 11 in which the animals are ruminants.

14. A method according to claim 11 in which the active compound is administered parenterally.

* * * * *